US009413130B2

(12) United States Patent
Hargis et al.

(10) Patent No.: US 9,413,130 B2
(45) Date of Patent: Aug. 9, 2016

(54) OPTICAL SYSTEMS

(71) Applicant: CVI LASER, LLC, Albuquerque, NM (US)

(72) Inventors: David E. Hargis, San Diego, CA (US); John O'Shaughnessy, Carlsbad, CA (US); Mark Lin, Carlsbad, CA (US); William Butterfield, Wildomar, CA (US)

(73) Assignee: CVI LASER, LLC, Albuquerque, NM (US)

( * ) Notice: Subject to any disclaimer, the term of this patent is extended or adjusted under 35 U.S.C. 154(b) by 199 days.

(21) Appl. No.: 14/103,709

(22) Filed: Dec. 11, 2013

(65) Prior Publication Data

US 2014/0160786 A1    Jun. 12, 2014

Related U.S. Application Data

(60) Provisional application No. 61/736,500, filed on Dec. 12, 2012.

(51) Int. Cl.
*F21V 29/00* (2015.01)
*H01S 3/02* (2006.01)
(Continued)

(52) U.S. Cl.
CPC .............. *H01S 3/025* (2013.01); *F21V 29/507* (2015.01); *G01N 21/255* (2013.01); *F21V 29/20* (2013.01); *G01N 2201/0231* (2013.01);
(Continued)

(58) Field of Classification Search
CPC ..... H01S 3/025; H01S 3/0071; H01S 3/0401; H01S 3/042; H01S 3/2391; G01N 21/255; G01N 2201/0231; F21V 29/00; F21V 29/20; F21V 29/40; F21V 29/50; F21V 29/502; F21V 29/54; F21V 29/402; F21V 29/507
See application file for complete search history.

(56) References Cited

U.S. PATENT DOCUMENTS 4,296,995 A    10/1981 Bickel
4,550,240 A    10/1985 Toida et al.
(Continued)

FOREIGN PATENT DOCUMENTS

DE    41 13 279    10/1992
DE    195 08 754    6/1999
(Continued)

OTHER PUBLICATIONS

Olympus Confocal Laser Scanning Biological Microscope, FV1000, Fluoview—Always Evolving, available at http://www.olympusamerica.com/files/seg_bio/fv1000_brochure.pdf.

*Primary Examiner* — Alan Cariaso
(74) *Attorney, Agent, or Firm* — Knobbe, Martens, Olson & Bear, LLP

(57) ABSTRACT

Various embodiments of the disclosure relate to an optical system that includes a base unit and one or more cartridges that are removably attachable to the base unit. The one or more cartridges can include optical components configured to output a beam of light (e.g., a laser). The base unit can be configured to combine multiple beams of light (e.g., emitted by multiple cartridges) and output a combined beam of light. The cartridges can be interchanged to modify the light output by the optical system. The optical system can include thermally one or more stable enclosures and/or a temperature controller. The optical system can include one or more alignment adjustment optical components configured to adjust the alignment of one or more light beams.

25 Claims, 11 Drawing Sheets

(51) Int. Cl.
*F21V 29/507* (2015.01)
*G01N 21/25* (2006.01)
*H01S 3/23* (2006.01)
*H01S 3/00* (2006.01)
*H01S 3/04* (2006.01)
*H01S 3/042* (2006.01)

(52) U.S. Cl.
CPC ............ *H01S 3/0071* (2013.01); *H01S 3/0401* (2013.01); *H01S 3/042* (2013.01); *H01S 3/2391* (2013.01)

(56) References Cited

U.S. PATENT DOCUMENTS

| | | |
|---|---|---|
| 4,573,465 A | 3/1986 | Sugiyama et al. |
| 4,632,554 A | 12/1986 | Pearce |
| 4,722,591 A | 2/1988 | Haffner |
| 4,817,101 A | 3/1989 | Wyeth et al. |
| 4,938,593 A | 7/1990 | Morris et al. |
| 4,983,042 A | 1/1991 | Korner et al. |
| 5,106,192 A | 4/1992 | Tucker et al. |
| 5,109,447 A | 4/1992 | Can |
| 5,147,349 A | 9/1992 | Johnson et al. |
| 5,152,759 A | 10/1992 | Parel et al. |
| 5,258,989 A | 11/1993 | Raven |
| 5,260,578 A | 11/1993 | Bliton et al. |
| 5,289,557 A | 2/1994 | Sheinis et al. |
| 5,295,143 A | 3/1994 | Rao et al. |
| 5,304,167 A | 4/1994 | Freiberg |
| 5,325,393 A | 6/1994 | Nighan, Jr. et al. |
| 5,343,038 A | 8/1994 | Nishiwaki et al. |
| 5,394,492 A | 2/1995 | Hwang |
| 5,446,532 A | 8/1995 | Yamazaki |
| 5,491,344 A | 2/1996 | Kenny et al. |
| 5,544,271 A | 8/1996 | Lim |
| 5,617,500 A | 4/1997 | Shionoya et al. |
| 5,633,695 A | 5/1997 | Feke et al. |
| 5,659,642 A | 8/1997 | King et al. |
| 5,668,903 A | 9/1997 | Neuberger et al. |
| 5,674,698 A | 10/1997 | Zarling et al. |
| 5,698,397 A | 12/1997 | Zarling et al. |
| 5,736,410 A | 4/1998 | Zarling et al. |
| 5,771,325 A | 6/1998 | Neuberger |
| 5,814,820 A | 9/1998 | Dong et al. |
| 5,823,942 A | 10/1998 | Toida |
| 5,824,269 A | 10/1998 | Kosaka et al. |
| 5,866,911 A | 2/1999 | Baer |
| 5,883,378 A | 3/1999 | Irish et al. |
| 5,952,668 A | 9/1999 | Baer |
| 6,048,444 A | 4/2000 | Takahashi et al. |
| 6,081,544 A | 6/2000 | Zamel et al. |
| 6,101,201 A | 8/2000 | Hargis et al. |
| 6,110,165 A | 8/2000 | Ota |
| 6,133,995 A | 10/2000 | Kubota |
| 6,175,440 B1 | 1/2001 | Conemac |
| 6,214,033 B1 | 4/2001 | Ii et al. |
| 6,215,807 B1 | 4/2001 | Reilly |
| 6,221,671 B1 | 4/2001 | Groner et al. |
| 6,222,961 B1 | 4/2001 | Engelhardt et al. |
| 6,462,345 B1 | 10/2002 | Simon et al. |
| 6,480,513 B1 | 11/2002 | Kapany et al. |
| 6,490,309 B1 | 12/2002 | Okazaki et al. |
| 6,510,001 B1 | 1/2003 | Engelhardt et al. |
| 6,557,369 B1 | 5/2003 | Phelps et al. |
| 6,592,822 B1 | 7/2003 | Chandler |
| 6,603,780 B2 | 8/2003 | Miyai |
| 6,614,031 B2 | 9/2003 | Engelhardt et al. |
| 6,654,165 B2 | 11/2003 | Engelhardt et al. |
| 6,677,566 B2 | 1/2004 | Knebel et al. |
| 6,737,635 B2 | 5/2004 | Engelhardt et al. |
| 6,750,457 B2 | 6/2004 | Heffelfinger et al. |
| 6,836,489 B2 | 12/2004 | Nishimura et al. |
| 6,867,899 B2 | 3/2005 | Knebel |
| 6,867,919 B2 | 3/2005 | Seyfried |
| 6,920,159 B2 | 7/2005 | Sidorin et al. |
| 6,958,470 B2 | 10/2005 | Hoffmann |
| 6,980,293 B1 | 12/2005 | Harada |
| 7,005,654 B2 | 2/2006 | Seyfried |
| 7,098,447 B2 | 8/2006 | Moellmann |
| 7,133,130 B2 | 11/2006 | Storz et al. |
| 7,151,633 B2 | 12/2006 | Storz et al. |
| 7,280,567 B2 | 10/2007 | Luo et al. |
| 7,280,570 B2 | 10/2007 | Seyfried et al. |
| 7,330,493 B2 | 2/2008 | Luo et al. |
| 7,394,063 B2 | 7/2008 | Schreiber |
| 7,426,027 B2 | 9/2008 | Noguchi et al. |
| 7,428,104 B2 | 9/2008 | Engelhardt |
| 7,430,231 B2 | 9/2008 | Luo et al. |
| 7,433,119 B2 | 10/2008 | Gugel |
| 7,457,300 B2 | 11/2008 | Luo et al. |
| 7,468,998 B2 | 12/2008 | Luo et al. |
| 7,474,462 B2 | 1/2009 | Ulrich et al. |
| 7,505,495 B2 | 3/2009 | Fratti et al. |
| 7,522,651 B2 | 4/2009 | Luo et al. |
| 7,535,937 B2 | 5/2009 | Luo et al. |
| 7,535,938 B2 | 5/2009 | Luo et al. |
| 7,542,489 B2 | 6/2009 | Luo et al. |
| 7,548,567 B2 | 6/2009 | Kupershmidt et al. |
| 7,564,624 B2 | 7/2009 | Leimbach et al. |
| 7,599,115 B2 | 10/2009 | Gugel |
| 7,599,413 B2 | 10/2009 | Luo et al. |
| 7,606,273 B2 | 10/2009 | Zhu et al. |
| 7,633,979 B2 | 12/2009 | Luo et al. |
| 7,660,035 B2 | 2/2010 | Bohm et al. |
| 7,724,363 B2 | 5/2010 | Wachsmuth et al. |
| 7,733,932 B2 | 6/2010 | Faybishenko |
| 7,742,226 B2 | 6/2010 | Bewersdorf et al. |
| 7,813,390 B2 | 10/2010 | Luo et al. |
| 7,835,601 B2 | 11/2010 | Seyfried et al. |
| 7,899,105 B1 | 3/2011 | Hargis et al. |
| 7,903,706 B2 | 3/2011 | O'Shaughnessy et al. |
| 7,949,025 B2 | 5/2011 | Olea |
| 7,999,935 B2 | 8/2011 | Dyba |
| 8,238,389 B2 | 8/2012 | Hargis et al. |
| 8,403,543 B2 * | 3/2013 | Kim .................. F21K 9/30 362/294 |
| 8,794,802 B2 * | 8/2014 | Wu ................ F21V 15/013 362/362 |
| 8,975,572 B2 | 3/2015 | Hargis |
| 9,014,224 B2 | 4/2015 | O'Shaughnessy et al. |
| 2001/0017868 A1 | 8/2001 | Kraenert et al. |
| 2001/0021210 A1 | 9/2001 | Nakaya et al. |
| 2002/0061032 A1 | 5/2002 | Miura et al. |
| 2002/0097772 A1 | 7/2002 | Dautremont-Smith et al. |
| 2003/0058530 A1 | 3/2003 | Kawano |
| 2003/0214987 A1 | 11/2003 | Yamanaka et al. |
| 2004/0027631 A1 | 2/2004 | Nagano et al. |
| 2004/0210289 A1 | 10/2004 | Wang et al. |
| 2005/0180474 A1 | 8/2005 | Buchold et al. |
| 2005/0201441 A1 | 9/2005 | Seyfried et al. |
| 2005/0220458 A1 | 10/2005 | Kupershmidt et al. |
| 2005/0281298 A1 | 12/2005 | Kupershmidt et al. |
| 2006/0097188 A1 | 5/2006 | Seyfried |
| 2006/0239317 A1 | 10/2006 | Yoshida et al. |
| 2006/0245049 A1 | 11/2006 | Knebel |
| 2006/0273260 A1 | 12/2006 | Casstevens et al. |
| 2007/0024978 A1 | 2/2007 | Jackson et al. |
| 2007/0195850 A1 | 8/2007 | Schluter et al. |
| 2008/0025677 A1 | 1/2008 | Sasaki |
| 2008/0089369 A1 | 4/2008 | Luo et al. |
| 2009/0097507 A1 | 4/2009 | Zhu et al. |
| 2009/0257054 A1 | 10/2009 | Hargis et al. |
| 2009/0274176 A1 | 11/2009 | O'Shaughnessy et al. |
| 2009/0323203 A1 | 12/2009 | Adams et al. |
| 2010/0006772 A1 | 1/2010 | Gugel |
| 2010/0073757 A1 | 3/2010 | Birk et al. |
| 2010/0111768 A1 | 5/2010 | Banerjee et al. |
| 2010/0177375 A1 | 7/2010 | Seyfried |
| 2010/0232011 A1 | 9/2010 | Seyfried |
| 2011/0063832 A1 * | 3/2011 | Hu .................. F21V 29/83 362/235 |

(56) References Cited

U.S. PATENT DOCUMENTS

| | | |
|---|---|---|
| 2011/0134949 A1 | 6/2011 | O'Shaughnessy et al. |
| 2011/0222054 A1 | 9/2011 | Krishnamachari |
| 2011/0273768 A1 | 11/2011 | Krishnamachari et al. |
| 2012/0099318 A1* | 4/2012 | Liu .................. F21S 2/005 362/249.02 |
| 2016/0028210 A1 | 1/2016 | O'Shaughnessy et al. |

FOREIGN PATENT DOCUMENTS

| | | |
|---|---|---|
| JP | 07 318810 | 12/1995 |
| WO | WO 2010/065779 | 6/2010 |

* cited by examiner

OPTICAL SYSTEMS

CROSS-REFERENCE TO RELATED APPLICATIONS

This application claims the benefit under 35 U.S.C. §119 (e) of U.S. Provisional Patent Application No. 61/736,500, filed Dec. 12, 2012, and titled OPTICAL SYSTEMS, the entirety of which is hereby incorporated by reference and made a part of this specification for all that it discloses.

BACKGROUND

1. Field of the Disclosure

This disclosure generally relates to optical systems such as light sources for use in optical (e.g., fluorescent or spectroscopic) analysis of biological samples (e.g., through a flow cell), or confocal microscopy.

2. Description of the Related Art

Optical analysis of biological samples (e.g., using flow cells), such as laser-induced fluorescence, involves illuminating biological samples with light (e.g., laser light) in order to test samples which may, for example, be tagged with fluorescent dyes. Fluorescent dyes absorb light at certain wavelengths and in turn emit their fluorescence energy at a different wavelength. This emission can be detected to ascertain properties of the fluid in the flow cell. Illumination of the test samples may be provided by a light source such as a laser light source.

SUMMARY

The various embodiments discussed herein are disclosed by way of example, and the inventions are not limited to the particular implementations illustrated and described herein.

Various embodiments of the discloser relate to an optical system that can include a base unit having a thermally stable enclosure and a cartridge receiver. A cartridge can be removably attached (or attachable) to the cartridge receiver. The cartridge can include a thermally stable enclosure. The optical system can include a temperature controller configured to control the temperature in the thermally stable enclosure or platform of the base unit and/or configured to control the temperature in the thermally stable enclosure of the cartridge. In some embodiments, one or more optical components configured to output a beam of light can be disposed in the thermally stable enclosure of the cartridge. In some embodiments, a laser configured to output a beam of light can be disposed in the thermally stable enclosure of the cartridge.

The optical system can include one or more alignment adjustment optical components, which can be disposed in the thermally stable enclosure of the base unit (or of the cartridge) and can be configured to adjust the alignment of the light beam. In some embodiments, the one or more alignment adjustment optical components can move to adjust the alignment of the light beam in response to an alignment adjustment interface, which can be accessible from outside the thermally stable enclosure of the base unit and/or from outside the thermally stable enclosure of the cartridge. The alignment adjustment interface can include a rotatable element. The one or more alignment adjustment optical components can include a horizontal boresight adjuster, which can include a prism rotatable about a vertical axis. The one or more alignment adjustment optical components can include a vertical boresight adjuster, a two axis boresight adjuster, a Risley prism assembly, one or more parallel plates, or combinations thereof.

In some embodiments, the one or more alignment adjustment optical components are configured to adjust the alignment of the light beam by up to about plus or minus five milliradians. The one or more alignment adjustment optical components can be configured to adjust the alignment of the light beam by at least about plus or minus 0.1 milliradians. The one or more alignment adjustment optical components can be configured to adjust the alignment of the light beam by up to about plus or minus 0.5 milliradians and/or by at least about plus or minus 0.1 milliradians.

In some embodiments, the optical system can include a second cartridge removably attached (or attachable) to the cartridge receiver.

The one or more optical components configured to output a beam of light and disposed in the thermally stable enclosure of the cartridge can include a laser, a laser diode, a diode-pumped solid-state (DPSS) laser, a fiber laser, a collimated fiber-coupled laser, a fiber optic device, and/or a light-emitting diode (LED).

The one or more optical components configured to output a beam of light and disposed in the thermally stable enclosure of the cartridge can include a Risley prism assembly, one or more plane parallel plates, or combinations thereof.

The optical system can include one or more optical components configured to output a beam of light and disposed in the thermally stable enclosure of the base unit.

The optical system can include one or more light redirecting optical components configured to redirect the beam of light, wherein the one or more light redirecting optical components are disposed in the thermally stable enclosure of the base unit. The one or more light redirecting optical components can include a monolithic beam combiner prism. The one or more light redirecting optical components can include one or more dichroic mirrors. The one or more light redirecting optical components can be configured to combine a plurality of light beams.

The cartridge can include electronic circuitry configured to control a laser.

The optical system can include one or more springs configured to removably attach the cartridge to the base unit.

DETAILED DESCRIPTION

Although certain preferred embodiments and examples are disclosed herein, inventive subject matter extends beyond the specifically disclosed embodiments to other alternative embodiments and/or uses of the inventions, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence.

For purposes of contrasting various embodiments with the prior art, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain features and details that relate to various embodiments disclosed herein are disclosed in U.S. Patent Application Publication No. 2011/0134949 (hereinafter the "'949 Publication"), titled COMPACT, THERMALLY STABLE MULTI-LASER ENGINE, filed on Nov. 4, 2010, and published on Jun. 9, 2011, which is hereby incorporated by reference in its entirety and made a part of this specification for all that it discloses. Certain features and details that relate to various embodiments disclosed herein are disclosed in U.S. Patent Application Publication No. 2009/0257054 (hereinafter the "'054 Publication"), titled COMPACT, THERMALLY STABLE FIBER-OPTIC ARRAY MOUNTABLE TO FLOW CELL, filed on Apr. 3, 2009, and published on Oct. 15, 2009, which is hereby incorporated by reference in its entirety and made a part of this specification for all that it discloses.

Various embodiments disclosed herein provide optical systems (e.g., for use in fluorescent analysis) that allow for simple interchanging of the wavelengths of light output from the optical system. Various embodiments disclosed herein provided optical systems (e.g., for use in fluorescent analysis) that allow for simple field repairs that can be performed without having to perform time-consuming alignment of the light beams or opening a thermally stable enclosure on the system.

Figure 1:
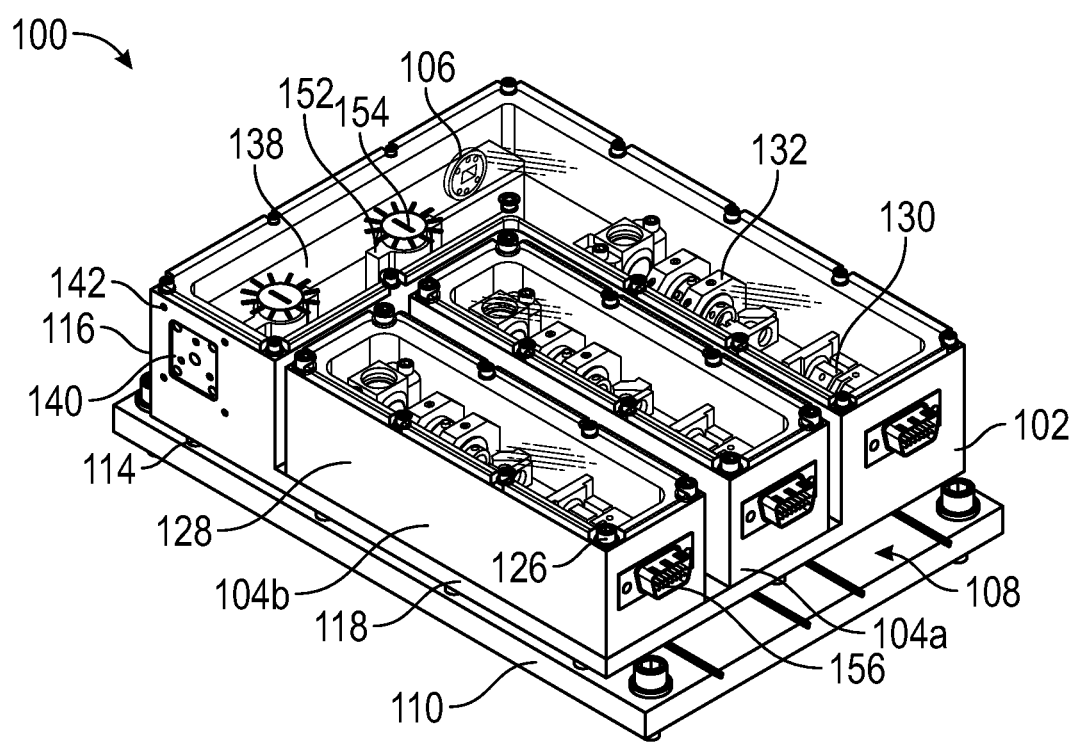
FIG. 1 is a perspective view of an example embodiment of an optical system, which can be a multi-laser system.
Figure 2:
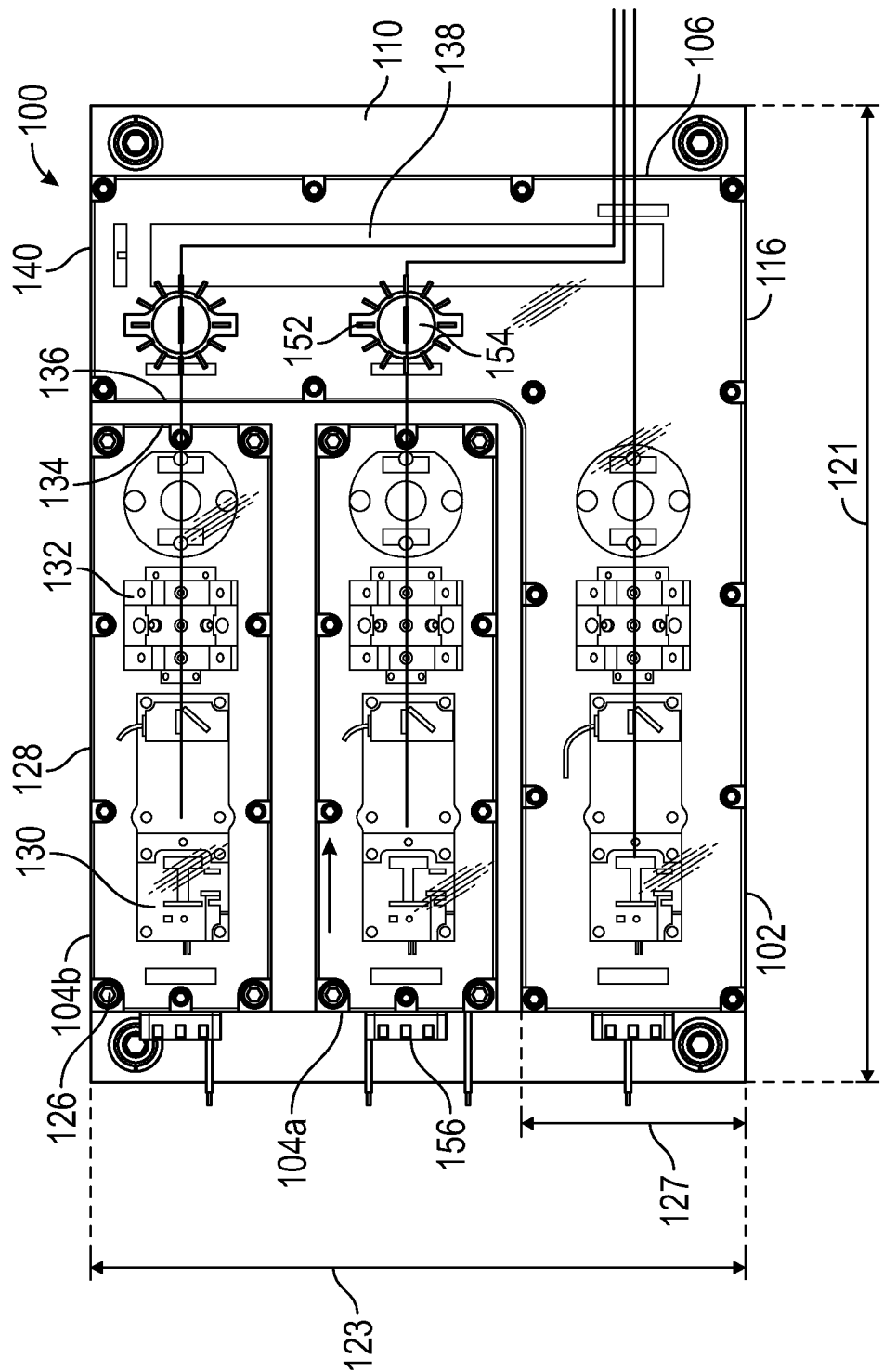
FIG. 2 is a top view of the optical system of FIG. 1.

FIG. 1 is a perspective view of an optical system 100, which can be a multi-laser system. FIG. 2 is a top view of the optical system 100. The optical system 100 can include a base unit 102 and one or more cartridges 104a and 104b removably attachable to the base unit 102. Although in the illustrated embodiment two cartridges 104a and 104b are shown, various other numbers of cartridges can be used (e.g., 1, 3, 4, 5, or more cartridges). The cartridges 104a and 104b can be configured to output a beam of light. For example, the cartridges 104a and 104b can include a laser source, such as a laser diode, a diode-pumped solid-state (DPSS) laser, a fiber laser, a collimated fiber-coupled laser, a fiber optic device, or an LED. In some embodiments, one or more of the cartridges 104a and 104b can be configured to receive light (e.g., a laser beam) from an external light source (e.g., an external laser) and can be configured to output the received light (e.g., to output the received laser beam). In some embodiments, one or more of the cartridges 104a and 104b can include a fiber optic collimator that outputs a beam of light. The optical system 100 can be configured to redirect one or more of the beams of light output from the cartridges 104a and 104b such that the light is output from an output 106 of the optical system 100. The light output from the output 106 can be directed to a target object (e.g., a flow cell (not shown)), or the light output from the output 106 can be coupled into an optical fiber (not shown) that directs the light towards the target object (e.g., a flow cell). In some embodiment, the target object (e.g., flow cell) can be coupled to the optical system 100 (e.g., at a position that is configured to intersect a beam of light emitted from the output 106). For example, the target object (e.g., flow cell) can be coupled to the base unit 102 (e.g., via one or more engagement elements 107 (e.g., screws), near the output 106) Various details relating to the coupling of a flow cell or other target object to an optical system configured to output light are disclosed in the '949 Publication and/or the '054 Publication In some embodiments, the optical system 100 can be configured to combine the beams of light output from two or more of the cartridges 104a and 104b.

Since the cartridges 104a and 104b are removable from the base unit 102, a cartridge 104a or 104b can be interchanged with a different cartridge that is configured to output light with different properties (e.g., a different wavelength of light). Accordingly, a single base unit 102 can be used with various different combinations of cartridges to produce various different combinations of light. To change the combination of light that is output from the optical system 100, the user does not need to perform time-consuming alignment of the light beams or open the enclosure and replace or adjust the optical components contained therein. Rather, the user can simply remove a cartridge from the base unit 102 and replace it with a different cartridge that is configured to output light of a different type (e.g., different wavelength). Also, a cartridge 104a or 104b can easily be replaced (e.g., if the cartridge 104a or 104b malfunctions or is otherwise in need of repair), without having to perform time-consuming alignment of the light beams or opening the enclosure. A field repair can be performed at the location of the optical system 100 by simply removing the defective cartridge 104a or 104b and replacing it with a replacement cartridge (e.g., configured to output light of the same wavelength). Then, the defective cartridge 104a or 104b can be discarded or can be brought to a repairing location for repair. Accordingly, field repairs can be performed more quickly and/or by personnel who are not necessarily trained to work on the actual optical components.

In some embodiments, the optical system 100 can include a temperature controller 108. In some embodiments, the temperature controller 108 can include a thermo electric cooler (TEC), one or more temperature sensors, and/or control electronics. In some embodiments, the temperature controller 108 can include a liquid temperature-controlled plate. In some embodiments, the temperature controller 108 can include an air temperature-controlled plate. In some embodiments, the temperature controller 108 can include a thermally conductive mounting surface whose temperature is controlled by the system into which the optical system 100 is installed into.

Various details and features relating to temperature controllers are disclosed in the '949 Publication and in the '054 Publication and can be incorporated or otherwise applied to the temperature controller 108 of FIG. 1 and the other embodiments disclosed herein. In some embodiments, the optical system 100 can include a base plate 110. The base plate 110 can function as a thermal heat sink for the temperature controller 108.

The base unit 102 can be spaced from the base plate 110 by a plurality of standoffs 114, which can be dispersed on the bottom of the bottom of the base unit 102 and/or on the top of the base plate 110. In some embodiments, the standoffs 114 can be low thermal conductivity standoffs. At least a portion of the temperature controller can be disposed between the base plate 110 and the base unit 102.

The base unit 102 can include an enclosure 116, which can contain optical components therein. The enclosure 116 can be a thermally stable, temperature controlled enclosure 116, and can have features similar to the enclosures disclosed in the '949 Publication and the '054 Publication. For example, the thermally stable and/or temperature controlled enclosure 116 can be configured such that the temperature inside the enclosure 116 is more stable than the ambient area outside the enclosure 116. In some embodiments, the temperature controller 108 can be configured to maintain the temperature within the enclosure 116 within a relatively small range (e.g., plus or minus 5 degrees Celsius, plus or minus 3 degrees Celsius, plus or minus 1 degree Celsius, or less, although ranges outside these values can be used in some implementations) of a target temperature, thereby insulating the optical components contained therein from the ambient environment and improving the optical performance, as discussed in the '949 Publication and the '054 Publication. In some embodiments, different components inside the enclosure 116 can have different coefficients of thermal expansion, and controlling the temperature inside the enclosure 116 (e.g., using the temperature controller 108) to maintain a relatively constant temperature therein can reduce the difference in expansion between components (e.g., to thereby facilitate the maintaining of proper alignment of the components). The enclosure 116 can include a thermally conductive (e.g., aluminum) housing that defines an internal chamber that houses the optical components. A cover plate can be attached to the housing to cover an opening that provides access to the internal chamber. In some embodiments, at least a portion of the enclosure 116 of the base unit 102 and/or the enclosures 128 of the cartridges 104a-d can be coated with a thermal insulating coating (e.g., which can be more thermally insulating than the walls of the enclosure 116 and/or 128. For example, some or all of the external surfaces of the enclosures 116 and 128, e.g., with the exception of the mounting surfaces that interface with the base unit 102, can be coated so as to reduce the thermal conductivity of the coated surfaces, thereby reducing the convective heat load on the optical system 100 due to changes in the ambient temperature.

Figure 3:
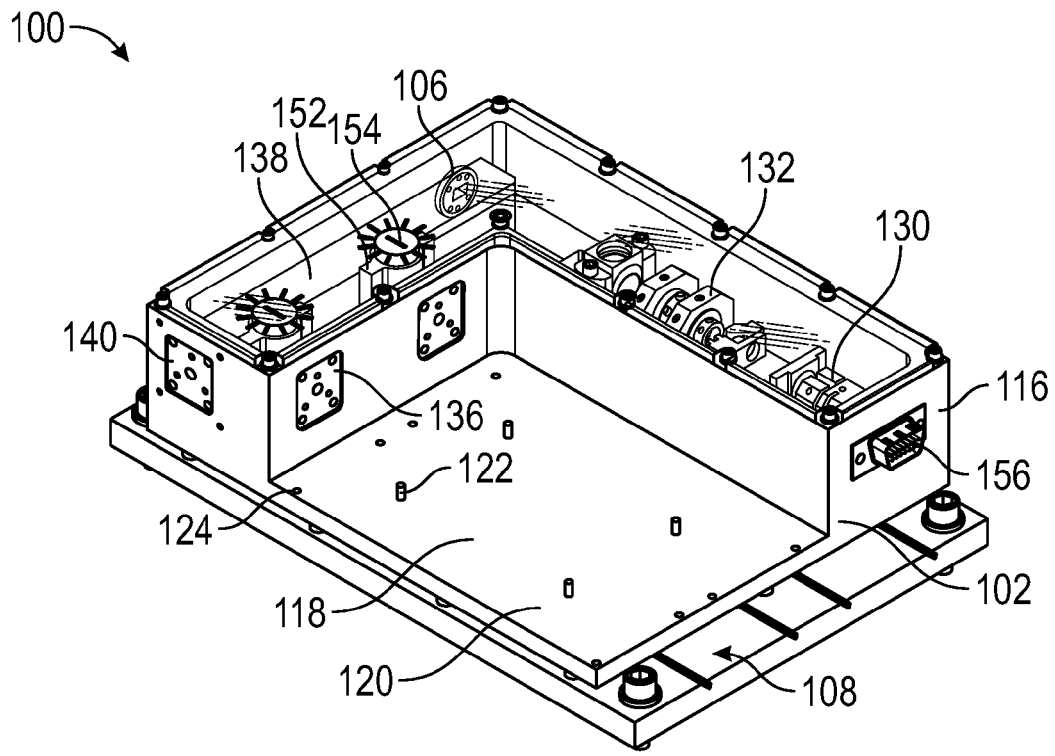
FIG. 3 is a perspective view of the optical system of FIG. 1 with the cartridges removed.

FIG. 3 is a perspective view of the optical system 100 with the cartridges 104a and 104b removed. The base unit 102 can include one or more cartridge receivers 118 configured to receive the cartridges 104a and 104b. The cartridge receiver 118 can include engagement features that are configured to engage corresponding engagement features on the cartridges 104a and 104b to removably attach the cartridges 104a and 104b to the base unit 102. The cartridge receiver 118 can be configured to receive multiple cartridges 104a and 104b in a side-by-side configuration (e.g., as shown in FIG. 1). Various other configurations are possible. The cartridge receiver 118 can include a first portion configured to receive a first cartridge 104a and a second portion configured to receive a second cartridge 104b. Additional cartridge receivers 118 or receiving portions can be included.

The cartridge receiver 118 can include a base member 120, which can provide a support surface on which one or more cartridges 104a and 104b can sit. The base member 120 can be made of a thermally conductive material (e.g., aluminum) and can be thermally coupled to the temperature controller 108. Thus, the cartridge receiver 118 can be configured to thermally couple the one or more cartridges 104a and 104b to the temperature controller 108 such that the temperature controller 108 can control the temperature inside the enclosures on the one or more cartridges 104a and 104b (e.g., in a manner similar to the temperature control performed for the enclosure 116 on the base unit 102). In some embodiments, the base member 120 can be integrally formed with the housing of the enclosure 116 on the base unit 102 (e.g., as a monolithic piece of thermally conductive material, such as aluminum). Other configurations are possible. For example, the base member 120 and/or other features of the cartridge receiver 118 can be formed separately from the enclosure 116 and can be coupled to the enclosure 116. In some embodiments, the temperature controller 108 can be configured to have different target temperatures for the different enclosures 116 and 128. In some embodiments, the different cartridges 104a and 104b can have different target temperatures. In some embodiments, multiple temperature controllers 108 can be used (e.g., to provide different temperatures for the different enclosures).

Various types of engagement features can be used to removably attach the one or more cartridges 104a and 104b to the base unit 102. With reference to FIG. 3, one or more pins 122 can be configured to engage one or more corresponding holes or slots (not shown) on the cartridges 104a and 104b (e.g., on the bottom thereof). In some embodiments two pins 122 can be configured to engage a single cartridge 104a or 104b. Although the cartridge can include two holes configured to receive the two pins 122, in some cases machining tolerances or other design variations can cause the pins 122 to not align properly with two holes that are both sized substantially the same as the pins 122. In some embodiments, the cartridge 104a or 104b can have a hole (not shown) that is sized substantially the same as the first pin, and the cartridge 104a or 104b can include a slot (not shown) configured to receive the second pin. The slot can be larger than the corresponding pin 122 in a first axis (which can be substantially parallel to the output path of the beam of light from the cartridge 104a and 104b), and the slot can be substantially the same size as the corresponding pin 122 in a second axis orthogonal to the first axis. The slot can accommodate for machining tolerances or other variations in the pins 122 and the holes and/or slots while substantially aligning the output beam of the cartridge 104a or 104b with a desired direction. Many variations are possible. For example, the cartridge receiver 118 can include one or more holes or slots that can be configured to receive one or more corresponding pins on the cartridge 104a or 104b.

The cartridge receiver 118 can include threaded holes 124 (e.g., formed on the base member 120). One or more screws 126 can be used to secure the one or more cartridges 104a and 104b to the cartridge receiver 118. For example, as can be seen in FIG. 1, screws 126 can extend through holes formed in the side walls of the housing of the cartridges 104a and 104b and can engage the threaded holes 124. In some embodiments, four screws 126 can secure a single cartridge 104a or 104b (e.g., positioned at the four corners thereof), but a different number of screws 126 can be used. Various other suitable engagement features can be used to attach the cartridges 104a and 104b to the base unit 102.

The one or more cartridges 104a and 104b can include an enclosure 128 that has optical components contained therein. The enclosure 128 can be formed by a housing that defines an internal chamber, and a cover plate can cover an opening to the internal chamber. The enclosures 128 of the cartridges 104a and 104b can include features similar to the enclosure 116 on the base unit 102 and similar to the enclosures described in the '949 Publication and the '054 Publication. The enclosures 128 of the one or more cartridges 104a and 104b can be thermally stable, temperature controlled enclosures 128. The housings of the enclosure 128 can be thermally conductive (e.g., made of aluminum), and can be thermally coupled to the temperature controller 108 (e.g., via the cartridge receiver 118), such that the temperature controller 108 can control the temperature within the enclosure 128 in a manner similar to the enclosure 116 on the base unit.

The cartridges 104a and 104b can include optical components that are configured to output a beam of light. For example, a cartridge 104a or 104b can include a laser 130 (e.g., a laser diode). The optical components of the cartridge 104a or 104b can be configured to adjust the alignment of the beam of light. For example, the cartridge 104a or 104b can include a Risley prism assembly 132 (e.g., having a Risley prism pair) and/or one or more plan parallel plates. Various other details and features relating to the optical components are disclosed in the '949 Publication and the '054 Publication. The optical components of the cartridge 104a or 104b can be pre-aligned to output the beam of light in a pre-aligned direction (e.g., substantially parallel to the longitudinal axis of the cartridge). The cartridge 104a or 104b can include a window 134, to allow the beam of light to exit the cartridge 104a or 104b. A corresponding window 136 can be included on the enclosure 116 of the base unit 102, to allow the beam of light to enter the enclosure 116 of the base unit 102.

The enclosure 116 can include one or more light redirecting optical components 138 configured to redirect one or more of the beams of light input into the enclosure 116 from the one or more cartridges 104a and 104b. The one or more light redirecting optical components 138 can be configured to direct the one or more light beams to the output 106, and in some embodiments, the one or more light redirecting optical components 138 can be configured to combine multiple beams of light (e.g., to provide a multi-wavelength output of light). By way of example, the one or more light redirecting optical components 138 can include a beam combiner, a beam combiner prism, a monolithic beam combiner prism, one or more dichroic mirrors, and/or other suitable light redirecting components. Various details relating to the light redirecting optical components 138 are disclosed in the '949 Publication and/or the '054 Publication.

In some embodiments, the enclosure 116 on the base unit 102 can include optical components that are configured to output a beam of light (e.g., a laser and a Risley prism assembly and/or one or more plane parallel plates similar to those of the cartridges 104a and 104b). The light beam generating optical components inside the enclosure 116 are not readily removable from the base unit 102, as are those of the cartridges 104a and 104b. In some implementations, a particular wavelength of light is used frequently, and is therefore included inside the enclosure 116. Wavelengths of light that are used less frequently can be produced by the light beam generating optical components contained in the cartridges 104a and 104b, so that they can be interchanged. In some embodiments, the light beam generating optical components contained in the enclosure 116 on the base unit 102 can be substantially aligned with the output 106 (e.g., as shown in FIG. 2).

Many other configurations are possible. For example, in some embodiments, the enclosure 116 on the base unit 102 can include multiple sets of light beam generating optical components (see FIGS. 4 and 5) and/or one or more of the cartridges 104a and 104b can include multiple sets of light beam generating optical components. In some embodiments, the enclosure 116 on the base unit 102 does not include any light beam generating optical components (see FIG. 6). In some embodiments, all of the light beams are input into the enclosure 116 from cartridges external to the enclosure 116. The embodiment of FIG. 6 includes four cartridges 104a-d. More cartridges or fewer cartridges may be included. Many configurations are possible, and any cartridge illustrated or described herein can include, or can be modified to include, features similar to any of the other cartridges illustrated or described herein.

By way of example, in some embodiments a laser can be included in the enclosure 116 that produces light between about 478 and about 498 nm, or of about 488 nm. The cartridges 104a and 104b can include lasers that are configured to produce light between about 395 nm and about 415 nm, or of about 405 nm, or between about 430 nm and about 450 nm, or of about 440 nm, or between about 505 nm and about 525 nm, or of about 515 nm, or between about 522 and about 542, or of about 532, or between about 551 and about 571, or of about 561, or between about 584 and about 604, or of about 594, between about 630 nm and about 650 nm, or of about 640 nm, between about 650 nm and about 670 nm or of about 660 nm, between about 670 nm and about 690 nm or of about 685 nm, between about 700 nm and about 750 nm or of about 730 nm and between about 750 nm and about 800 nm or of about 785 nm. Many variations are possible. For example, lasers configured to emit a light beam of any of the disclosed wavelengths (or any other suitable wavelength) can be included in the enclosure 116 or in the one or more cartridges 104a and 104b.

In some embodiments, the optical system 100 can be compact. For example, the optical system 100 can have a length 121 of about 8.7 inches, at least about 6 inches, at least about 7 inches, at least about 8 inches, or at least about 9 inches. In some cases, the length 121 of the optical system can be less than or equal to about 12 inches, less than or equal to about 10 inches, less than or equal to about 9 inches, less than or equal to about 8 inches, or less than or equal to about 7 inches. The optical system 100 can have a width 123 of about 5.8 inches, about 7.6 inches, or about 7.8 inches. In some cases, the optical system 100 can have a width 123 of at least about 3 inches, at least about 4 inches, at least about 5 inches, at least about 6 inches, or at least about 7 inches. In some cases, the width 123 of the optical system 100 can be less than or equal to about 12 inches, less than or equal to about 10 inches, less than or equal to about 8 inches, less than or equal to about 7 inches, less than or equal to about 6 inches, or less than or equal to about 5 inches. The optical system 100 can have a height 125 of about 2.5 inches. In some cases, the height 125 of the optical system 100 can be at least about 1 inch, at least about 1.5 inches, at least about 2 inches, at least about 2.5 inches, or at least about 3 inches. In some cases, the height 125 of the optical system 100 can be less than or equal to about 5 inches, less than or equal to about 4 inches, less than or equal to about 3 inches, less than or equal to about 2.5 inches, or less than or equal to about 2 inches. In some embodiments, the optical system 100 can occupy a volume of about 170 cubic inches, of 169.65 cubic inches, of about 165 cubic inches, of 165.3 cubic inches, of about 126 cubic inches, or of 126.15 cubic inches. The optical system 100 can occupy a volume between about 126.15 cubic inches and about 169.65 cubic inches. In some cases the optical system 100 can occupy a volume of at least about 70 cubic inches, at least about 90 cubic inches, at least about 100 cubic inches, at least about 120 cubic inches, at least about 140 cubic inches, at least about 160 cubic inches, or at least about 170 cubic inches. In some cases the optical system 100 can occupy a volume of less than or equal to about 250 cubic inches, less than or equal to about 225 cubic inches, less than or equal to about 200 cubic inches, less than or equal to about 175 cubic inches, less than or equal to about 150 cubic inches, less than or equal to about 125 cubic inches, or less than or equal to about 100 cubic inches. The enclosure 116 of the base unit 102 can have a width 127 of about 2 inches, at least about 1 inches, at least about 1.5 inches, at least about 2 inches, less than or equal to about 5 inches, less than or equal to about 4 inches, less than or equal to about 3 inches, less than or equal to about 2 inches, or less than or equal to about 1.5 inches. A cartridge 104*a*-*c* can have a width 129 of about 1.6 inches, at least about 1 inches, at least about 1.5 inches, at least about 2 inches, less than or equal to about 5 inches, less than or equal to about 4 inches, less than or equal to about 3 inches, less than or equal to about 2 inches, or less than or equal to about 1.5 inches. A cartridge 104*a*-*c* can have a length 131 of about 5.2 inches, at least about 3 inches, at least about 4 inches, at least about 5 inches, at least about 6 inches, less than or equal to about 8 inches, less than or equal to about 7 inches, less than or equal to about 6 inches, or less than or equal to about 5 inches. In some cases a cartridge 104*a*-*c* can occupy a volume of at least about 5 cubic inches, at least about 10 cubic inches, at least about 15 cubic inches, less than or equal to about 30 cubic inches, less than or equal to about 25 cubic inches, less than or equal to about 20 cubic inches, less than or equal to about 15 cubic inches, or less than or equal to about 10 cubic inches. In some embodiments, the optical system 100 and the components thereof can have dimensions outside those ranges and values that are specifically discussed herein.

In some embodiments, as shown in FIGS. 1-3, the enclosure 116 on the base unit 102 can include one or more additional windows 140 to receive light from additional sources (e.g., other than a cartridge). For example, in some embodiments, a fiber optic input port, which may include a fiber optic collimator, can be coupled to the enclosure 116 to input a beam of light into the enclosure 116 through the window 140. In some embodiments, the enclosure 116 can include threaded holes 142 configured to receive screws that can be used to mount a fiber optic collimator and/or to adjust the alignment of the beam of light from the fiber optic collimator. The fiber optic collimator can collimate light received from a fiber optic cable that receives light from an external light source (e.g., an external laser).

Figure 7:
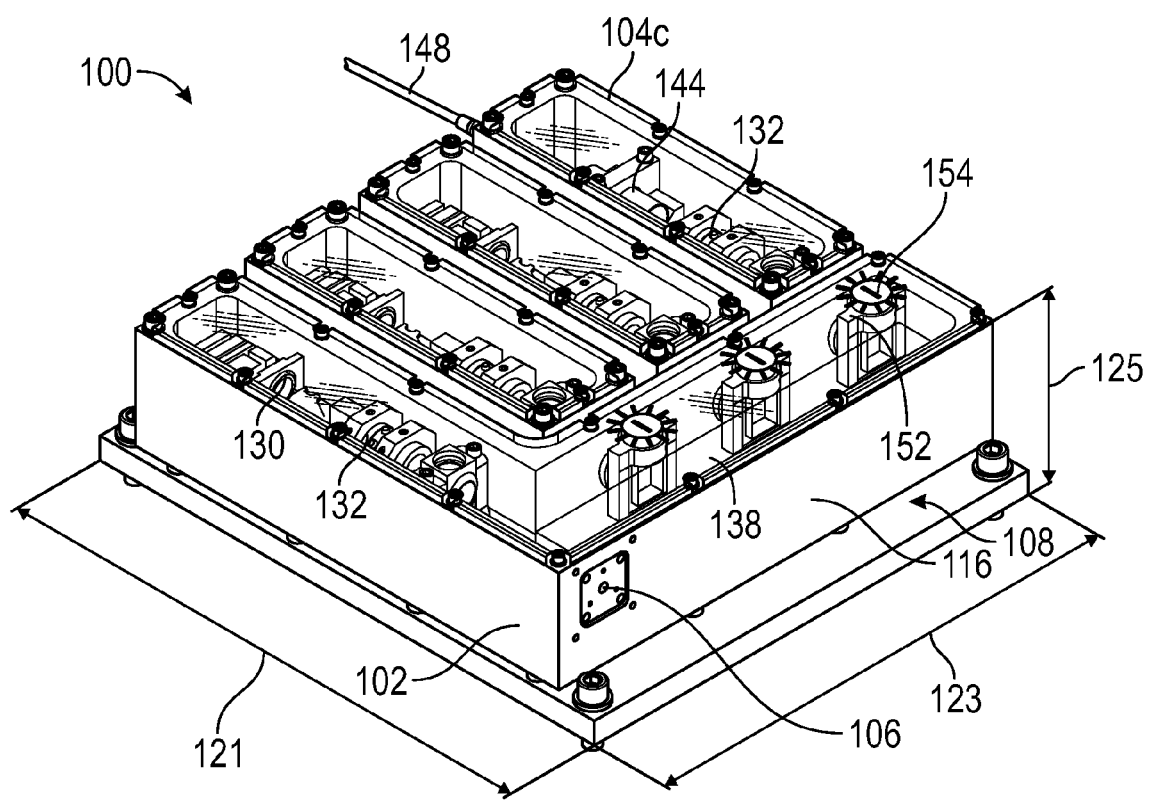
FIG. 7 is a perspective view of another example embodiment of an optical system.
Figure 8:
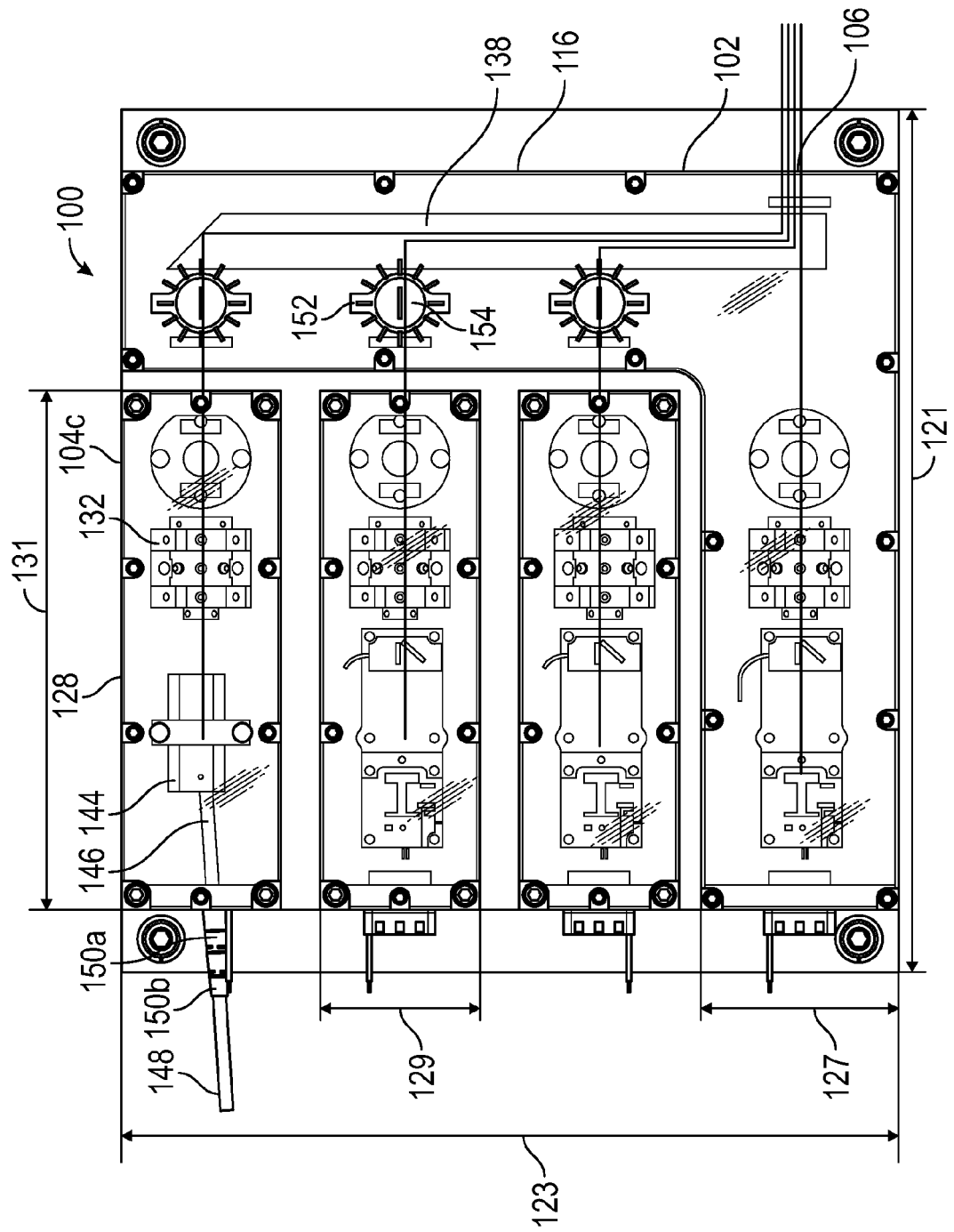
FIG. 8 is a top view of the optical system of FIG. 7.

With reference to FIGS. 7 and 8, in some embodiments a cartridge 104*c* can include a fiber optic input and a fiber optic collimator 144 (e.g., instead of a laser inside the cartridge 104*c*). The cartridge 104*c* can have features similar to the other cartridges described herein. For example, a Risley prism assembly 132 and/or one or more plane parallel plates can be included in the cartridge 104*c* to align the light beam output by the fiber optic collimator 144. The fiber optic collimator 144 can collimate light received from a fiber optic cable 146 (e.g., such that the cartridge 104*c* is configured to output a beam of light). In some embodiments, an external fiber optic cable 148 can be optically coupled to an internal fiber optic cable 146 to deliver light from an external light source (e.g., an external laser) to the fiber optic collimator 144. For example, the internal fiber optic cable 146 can be coupled to a first optical coupler 150*a*, which can be configured to optically couple with a second optical coupler 150*b* at the end of the external fiber optic cable 148. The first coupler 150*a* can be configured to direct the light from outside the enclosure 128 of the cartridge 104*c* to the inside of the enclosure 128. The housing of the enclosure 128 can be sealed around the first optical coupler 150*a* to prevent moisture and contaminants from entering the enclosure as well as to help maintain thermal stability inside the enclosure 128. Other arrangements are possible. Even though the embodiment of FIGS. 7 and 8 show only one of the cartridges 104*c* as being configured to receive light from a fiber optic cable, various other cartridges discussed and illustrated herein can be modified to receive light from fiber optic cable (e.g., similar to the cartridge 104*c*). Various additional features and details relating to providing light from an external source via a fiber optic cable are disclosed in the '949 Publication and/or the '054 Publication.

Figure 9:
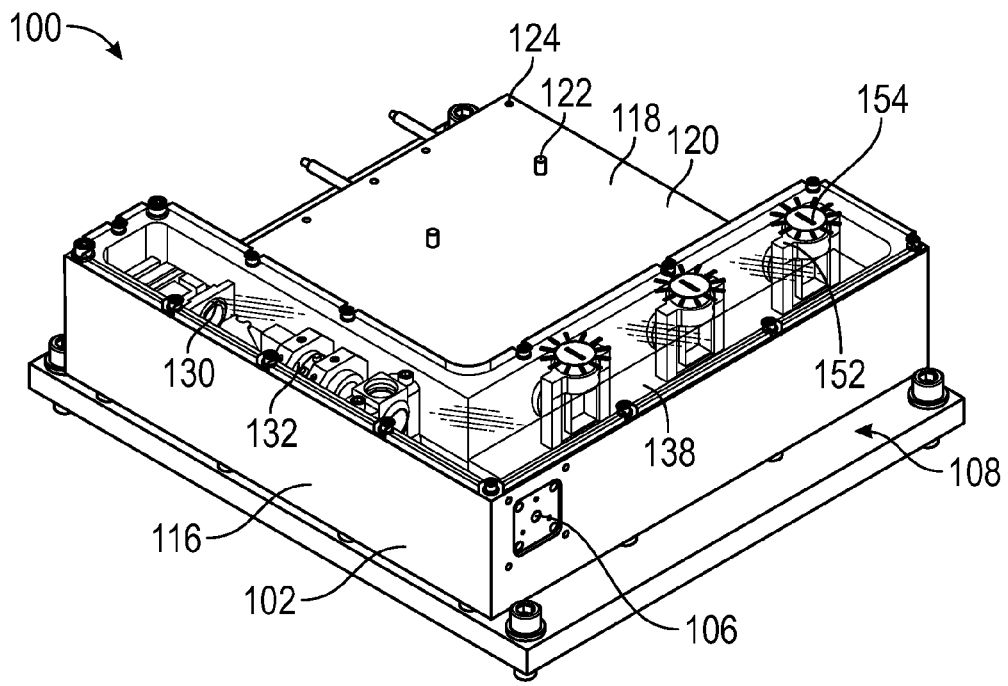
FIG. 9 is a perspective view of an example embodiment of an optical system that can be used without any cartridges attached thereto.
Figure 10:
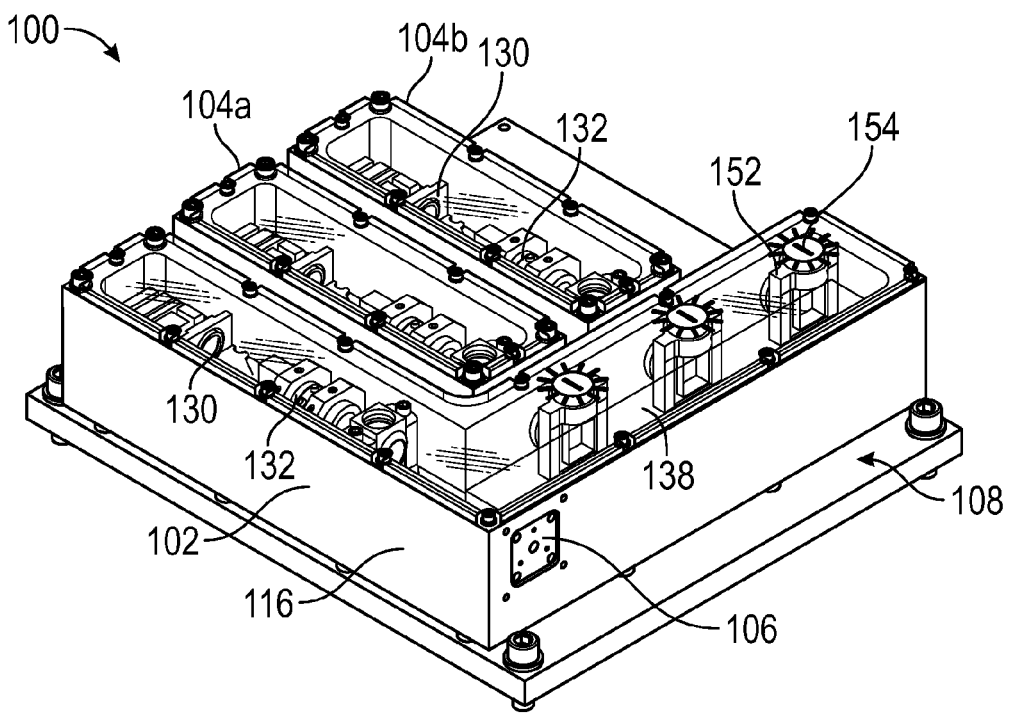
FIG. 10 is a perspective view of an example embodiment of an optical system that can be used to combine light from three light sources.
Figure 11:
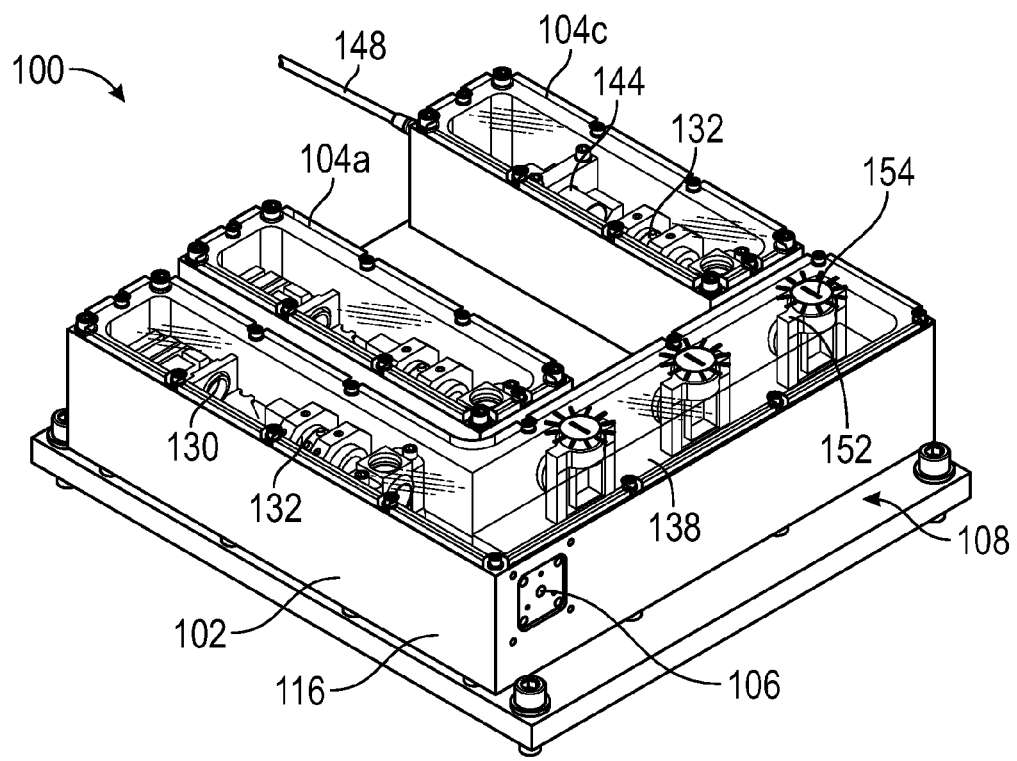
FIG. 11 is a perspective view of another example embodiment of an optical system that can be used to combine light from three light sources.
Figure 12:
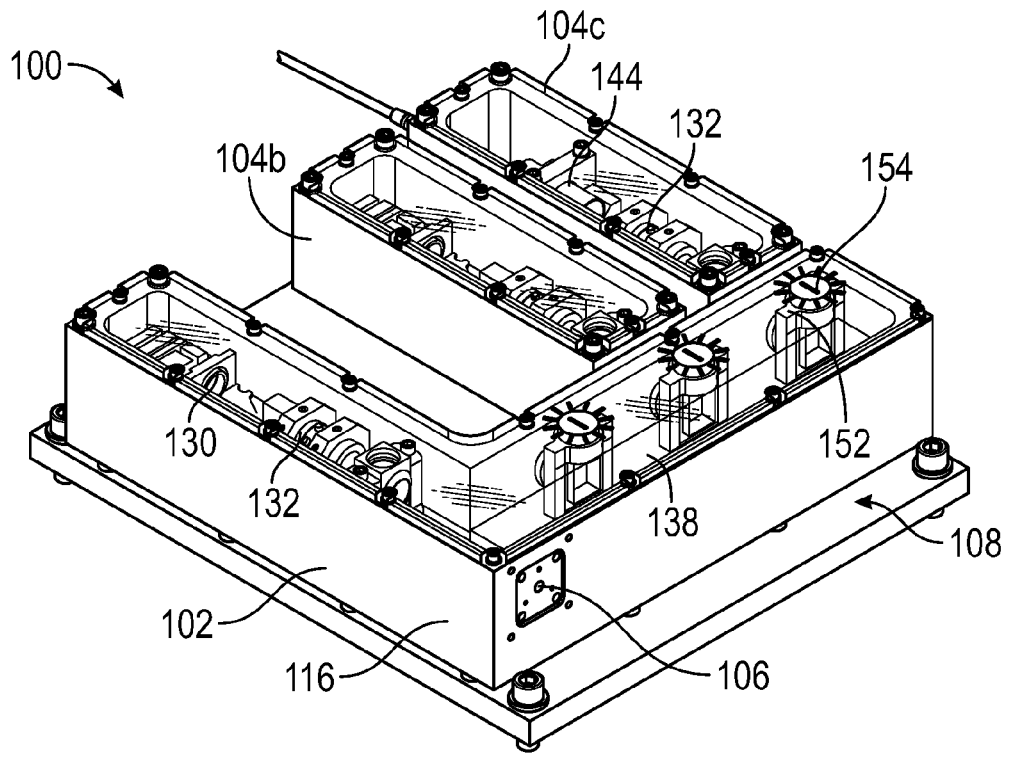
FIG. 12 is a perspective view of another example embodiment of an optical system that can be used to combine light from three light sources.

The optical system 100 can be used in various different configurations (e.g., with various different combinations of cartridges). For example, FIG. 9 shows an example embodiment in which the optical system 100 can be used to output light (e.g., of about 488 nm) from only the light beam generating optical components contained in the enclosure 116 on the base unit 102. Thus, the optical system 100 shown in FIG. 9 can be used without any cartridges attached thereto. FIG. 10 shows an example embodiment in which the optical system 100 can be used to combine light from three light sources (e.g., about 488 nm, about 440 nm and/or about 405 nm, about 640 nm, about 660 nm, about 685 nm, and/or about 730 nm and/or about 785 nm). In the embodiment of FIG. 10, two cartridges 104*a* and 104*b* can be attached to the base unit 102, and a third receiving portion of the cartridge receiver 118 is left empty. FIG. 11 shows an example embodiment in which the optical system 100 can be used to combine three light beams (e.g., about 488 nm, about 405 nm or about 440 nm, and about 532 nm, about 561 nm, or about 594 nm). In the embodiment of FIG. 11, the cartridges 104*a* and 104*c* are attached to the base unit 102 and the cartridge 104*b* is removed. FIG. 12 shows an example embodiment in which the optical system 100 can be used to combine three light beams (e.g., about 488 nm, about 640 nm, and about 532 nm, about 561 nm, or about 594 nm). In the embodiment of FIG. 12, the cartridges 104*b* and 104*c* are attached to the base unit 102 and the cartridge 104*a* is removed. Many other configurations are possible.

In some embodiments, one or more alignment adjustment optical components can be included in the enclosure 116 of the base unit 102. The alignment adjustment optical components can be configured to adjust the alignment of the one or more light beams that enter the enclosure 116 from the one or more cartridges 104*a* and 104*b* (e.g., before the one or more light beams are redirected by the one or more light redirecting optical components 138). Although the optical components of the cartridges 104*a* and 104*b* can be pre-aligned to direct the emitted beam of light in substantially a desired direction, the alignment of the one or more light beams may need to be adjusted slightly due to manufacturing tolerance and other slight variations (e.g., on the interface between the cartridges 104*a* and 104*b* and the base unit 102, or in the beam combiner prism 138). The alignment adjustment optical components inside the enclosure 116 can enable a user to make fine adjustments to the alignment of the one or more light beams to accommodate for the machining tolerances and other slight variations mentioned above.

In some embodiments, the alignment adjustment optical components can include one or more horizontal boresight adjusters 152. For example, a horizontal boresight adjuster 152 can be included for each cartridge receiving portion on the base unit 102 (e.g., behind each window 136). Thus, a horizontal boresight adjuster 152 can be positioned in the path of one or more or all of the light beams entering the enclosure 116 from the cartridges 104a and 104b. The horizontal boresight adjuster 152 can be configured to make fine adjustments to the alignment of the light beam in the horizontal direction. For example, the horizontal boresight adjuster 152 can include a prism (e.g., a thin prism) that can be configured to rotate about a vertical axis to thereby adjust the horizontal alignment of the light beam.

The alignment adjustment optical component (e.g., horizontal boresight adjuster 152) can move (e.g., rotate) in response to an alignment adjustment interface 154 that is accessible from outside the enclosure. The alignment adjustment interface 154 can include a rotatable element, which can have, for example, a slot formed therein to receive a screw driver to allow a user to rotate the rotatable element. In some embodiments, the rotatable element can have a thumb screw to allow rotation of the rotatable element without a screwdriver or other tools. The rotatable elements can be at least partially disposed in holes in the cover plate for the enclosure 116. In some embodiments, the top of the rotatable elements can be substantially flush with the top of the cover plate.

Gears can be included such that rotation of the rotatable element causes a lesser degree of rotation on the horizontal boresight adjuster 152, which can enable a user to perform very fine adjustments of the alignment. In some embodiments, the horizontal boresight adjuster 152 can be configured to provide adjustment of the angle of the light beam by at least about plus or minus 0.1 milliradians, or by at least about plus or minus 0.25 milliradians, or by about plus or minus 0.25 milliradians to about plus or minus 1 milliradian, or by up to about plus or minus 0.5 milliradian, or by up to about plus or minus 1.0 milliradians, or by up to about plus or minus 2.0 milliradians, or by up to about plus or minus 5 milliradians. The boresight adjuster 152 can provide for very precise adjustment to the alignment of the light beam, but only across a small range of adjustment.

In some embodiments, vertical boresight adjusters (not shown) can be included. The vertical boresight adjusters can be positioned either in front or behind the horizontal boresight adjusters 152 such that the light beams interact first with a boresight adjuster for one axis and then the boresight adjuster for the other axis. The vertical boresight adjusters can include features similar to the horizontal boresight adjusters 152 described herein, and can function in a similar manner. In some embodiments, an alignment adjustment interface similar to that of the horizontal boresight adjuster 152 can be used to enable a user to adjust the vertical boresight adjuster from outside the enclosure. For example, a rotatable element can be at least partially disposed in a hole in the cover plate of the enclosure. Gears can be included, such that rotation of the rotatable element about a vertical axis is translated to rotation of the prism for the vertical boresight adjuster about a horizontal axis.

Various other types of alignment adjustment optical components can be used and can be controlled by an alignment adjustment interface (that can be accessible from outside the enclosure). In some embodiments, the enclosure 116 can include a two axis boresight adjuster to adjust the alignment of a light beam input from a cartridge. The two axis boresight adjuster can include a prism (e.g., a thin prism) that is configured to be rotated about a horizontal axis and also about a vertical axis in response to an alignment adjustment interface (that is accessible from outside the enclosure), such that a single boresight adjuster can adjust the alignment in both the horizontal and vertical directions. In some embodiments, a Risley prism assembly (e.g., having a Risley prism pair) can be included in the enclosure 116 for adjusting the alignment of the light beam input from a cartridge 104a or 104b. An alignment adjustment interface can be accessible from outside the enclosure 116 to enable the Risley prism assembly to be adjusted by a user to modify the alignment of the light beam. In some embodiments one or more plane parallel plates can be included in the enclosure 116 for adjusting the light beam input from a cartridge 104a or 104b. An alignment adjustment interface can be accessible from outside the enclosure 116 to enable the one or more plane parallel plates to be adjusted by a user to modify the alignment of the light beam. In some embodiments, one or more of the cartridges 104a and/or 104b can include an alignment adjustment interface that is accessible from outside the enclosure 128 (e.g., similar to the alignment adjustment interface 154), which can be used to adjust one or more alignment adjustment optical components (e.g., a horizontal boresight adjuster, a vertical boresight adjuster, a two axis boresight adjuster, a Risley prism assembly, and/or one or more plane parallel plates, etc.) that are inside the cartridge 104a or 104b.

Figure 4:
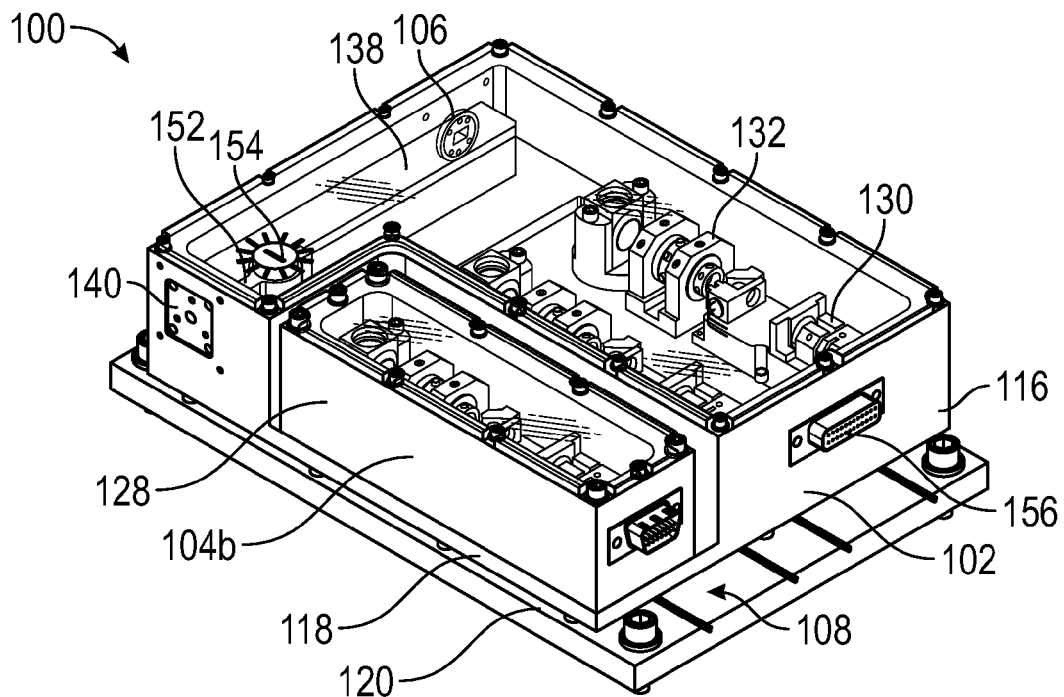
FIG. 4 is a perspective view of another example embodiment of an optical system.
Figure 5:
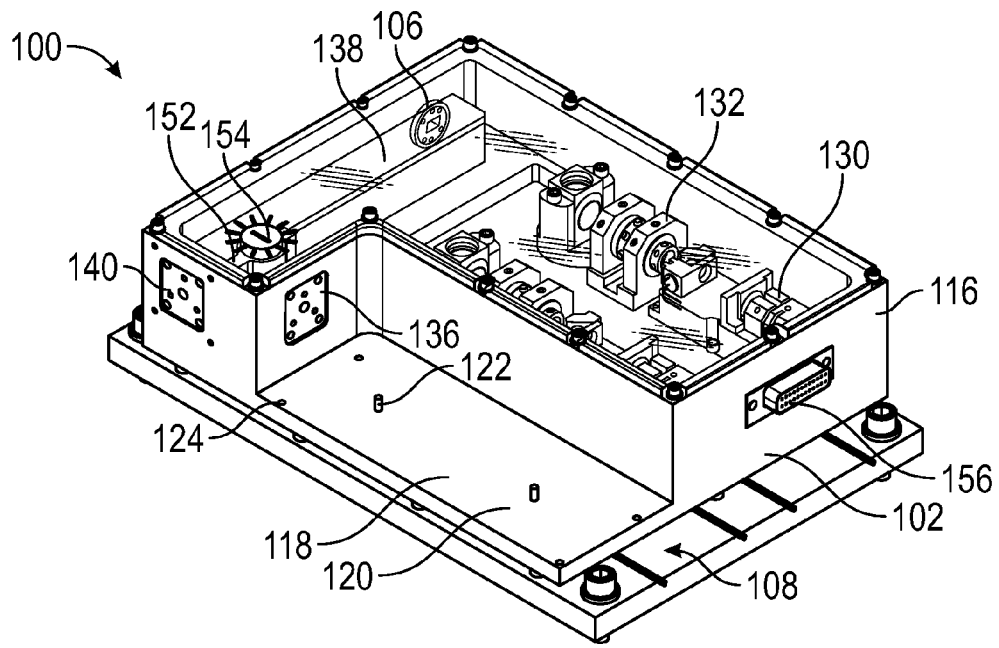
FIG. 5 is a perspective view of the optical system of FIG. 4, with a cartridge removed.
Figure 6:
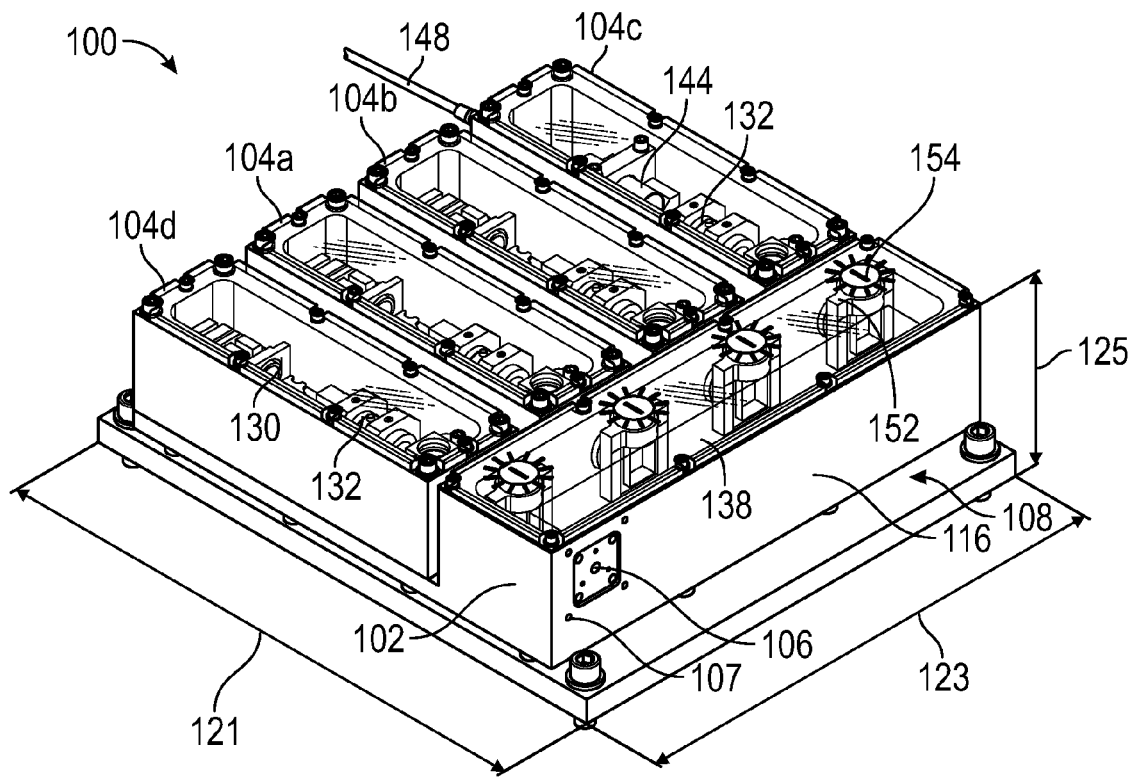
FIG. 6 is a perspective view of another example embodiment of an optical system.

The one or more cartridges 104a and 104b can include an input 156. The input can be a D-sub connector, or other suitable connector. In some embodiments, the input 156 can receive power from an external power source, and the power can be delivered to the light source (e.g., laser diode) in the cartridge. In some embodiments, the input 156 can receive control information from an external controller. In some embodiments, the input 156 can also provide feedback information (e.g., automatic power control (APC) information and/or overdrive protection information) to the external controller. In some embodiments, some or all of the electronics for the laser can be included in or on the cartridge 104a or 104b itself. For example, a mirror can deliver a small percentage of the emitted light to an optical sensor (e.g., a photodiode) to measure the light being emitted and generate APC information, which can be used by electronics in or on the cartridge 104a or 104b to control the power delivered to the laser 130. In some embodiments, the input 156 does not provide any output information, and in some cases only receives power. If multiple light sources are included inside the enclosure 116 on the base unit 102, the light sources can share an input (as shown in FIGS. 4 and 5), or each light source can have a dedicated input.

Figure 13:
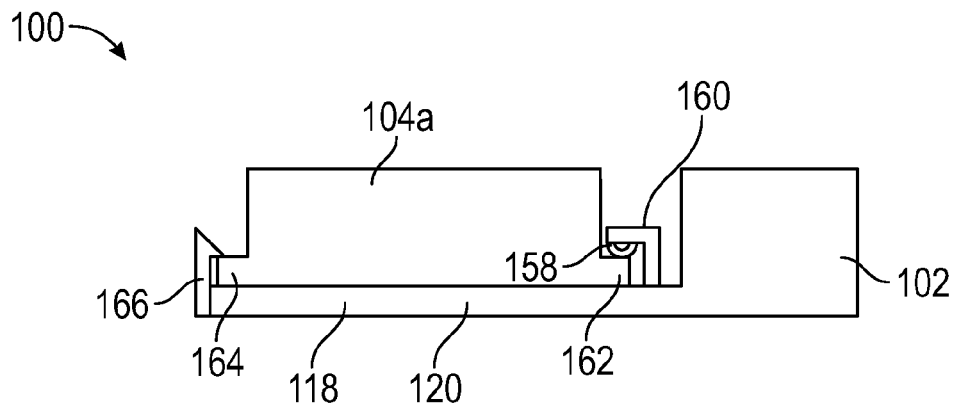
FIG. 13 is a semi-schematic side view of an example embodiment of engagement features for securing a cartridge to a base unit of an optical system.

FIG. 13 is a semi-schematic side view of an example embodiment of engagement features for securing a cartridge 104a to a base unit 102. The cartridge 104a can sit on the base member 120 of the base unit 102. One or more springs 158 (e.g., leaf springs) can be included on a first side (e.g., front) of the cartridge receiving portion. The springs 158 can be suspended over a gap by one or more support members 160, or the springs 158 can be attached to the base member 120 or other portion of the base unit 120 can form a gap. One or more springs 166 (e.g., arm springs) can be included on a second side (e.g., back) of the cartridge receiving portion. The spring 166 can include a flexible arm and a clipping portion. An engagement portion 162 (e.g., a lip) on the first side of the cartridge 104a can be inserted into the gap formed by the spring 158, thereby causing the spring 158 to flex and apply a force onto the cartridge 104a. The second side of the cartridge 104a can be lowered to engage the spring 166. The spring 166 can have an angled surface that causes the arm to flex as the second side of the cartridge 104a is lowered. Once an engagement portion 164 (e.g., lip) clears the clipping portion of the spring 166, the spring clips into place with the clipping portion over the engagement portion 164 to secure the cartridge 104a to the base unit 102. In some embodiments, the cartridge 104a can include two slots (e.g., formed on the bottom thereof) to receive the two pins 122 shown in FIG. 3, for positioning the cartridge 104a. In some embodiments a non-spring clamp can be used in place of the spring 166. For example, a clamp can be rotatable (or otherwise movable) to a position that engages the engagement portion 164 on the second side of the cartridge 104a.

The engagement features of FIG. 13 can enable a user to remove and attach a cartridge 104a without any tools, and in less time as compared to engagement features using screws. Also, the contact force between the cartridge 104a and the base unit 102 can be predetermined by the one or more springs 158 and/or the one or more springs 166. Accordingly, the contact force between the cartridge 104a and the base unit 102 is not determined by the user (e.g., as can be the case when screws are used). Accordingly, attachment of the cartridge 104a to the base unit 102 can be further simplified, as compared to a system involving screws, because the user does not need to apply a particular torque value to achieve a desired contact force between the cartridge 104a and the base unit 102. A known contact force between the cartridge 104a and the base unit 102 can facilitate the control of the heat transfer through the interface between the cartridge 104a and the base unit 102.

Figure 14:
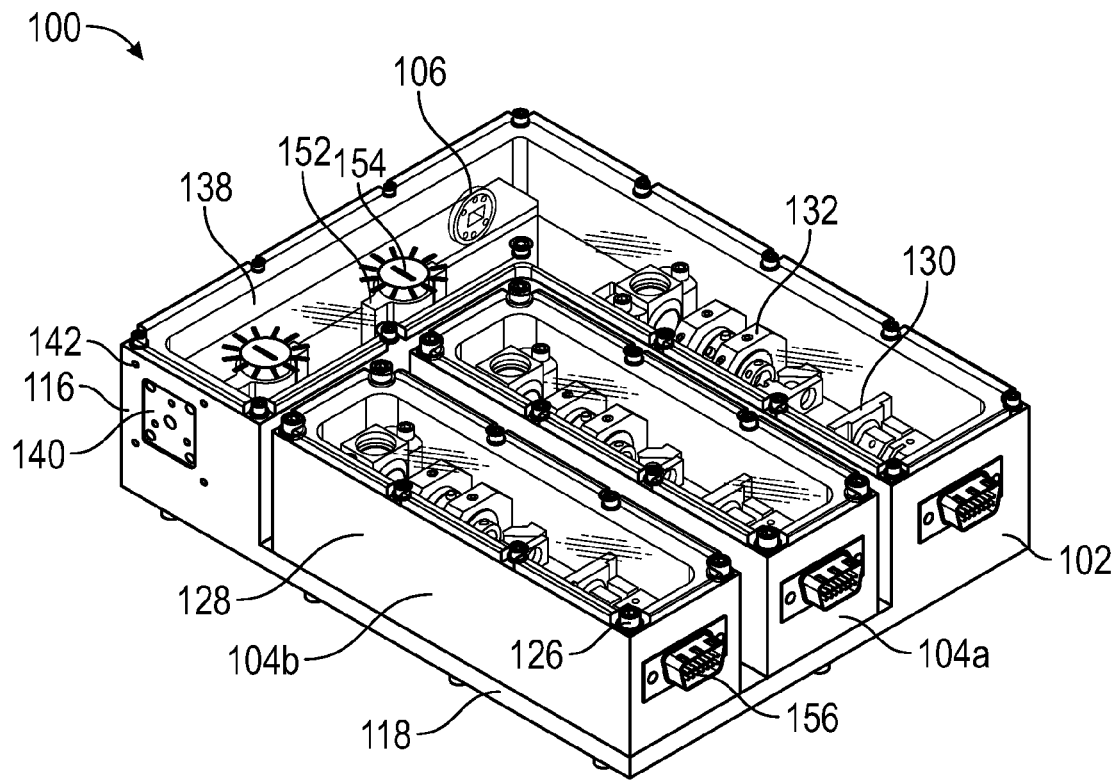
FIG. 14 is a perspective view of another example embodiment of an optical system.

With reference to FIG. 14, in some embodiments, the optical system 100 can be provided separate from the thermoelectric cooler (TEC), or other temperature controller 108. For example, the optical system 100 of FIG. 14 can include a base unit 102 having a thermally stable enclosure 116 and a cartridge receiver 118. The one or more cartridges 104a-b can include thermally stable enclosures 116, which can be removably attachable to the cartridge receiver 118. The base unit 102 can be configured to interface with an external temperature controller (not shown in FIG. 14) to transfer heat to or from the enclosures 116 and/or 104a-b to thereby regulate the temperature inside the enclosures 116 and/or 104a-b. The external temperature controller can be part of a larger system (e.g., which can be configured to control the temperature of additional components in addition to the optical system 100).

Figure 15:
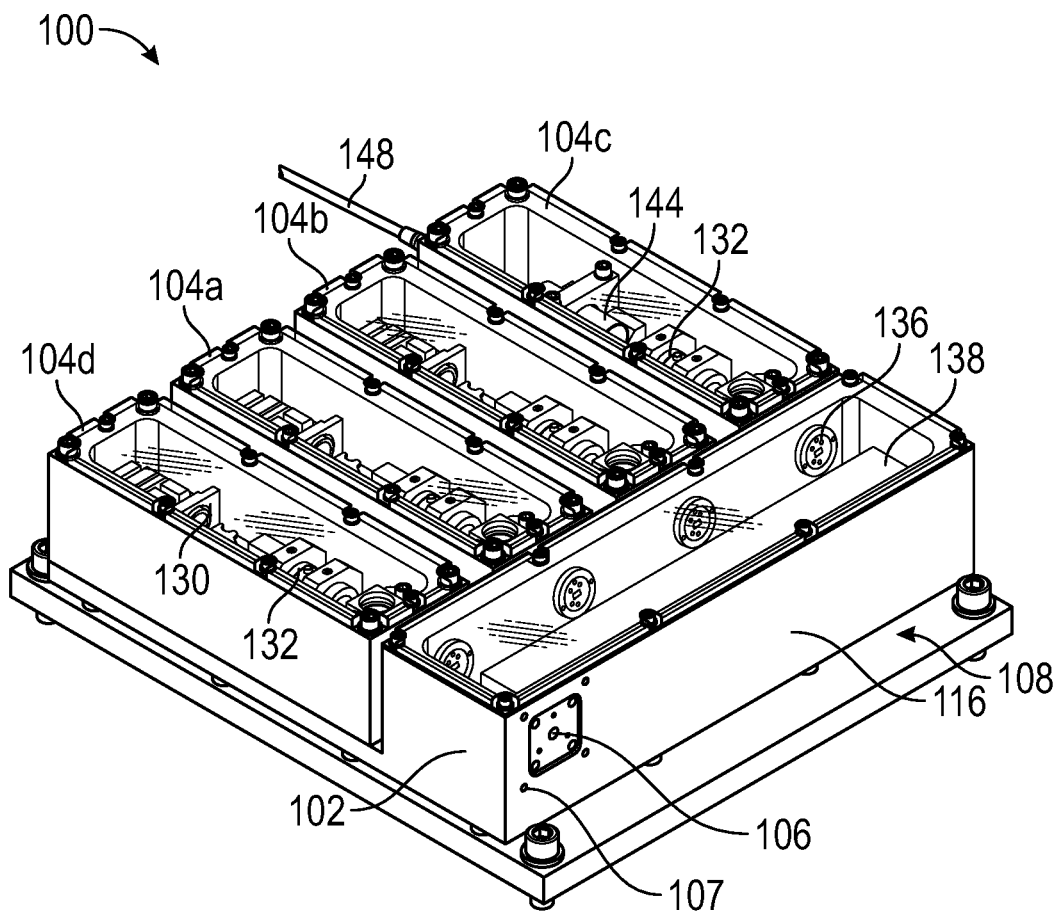
FIG. 15 is a perspective view of another example embodiment of an optical system.
Figure 16:
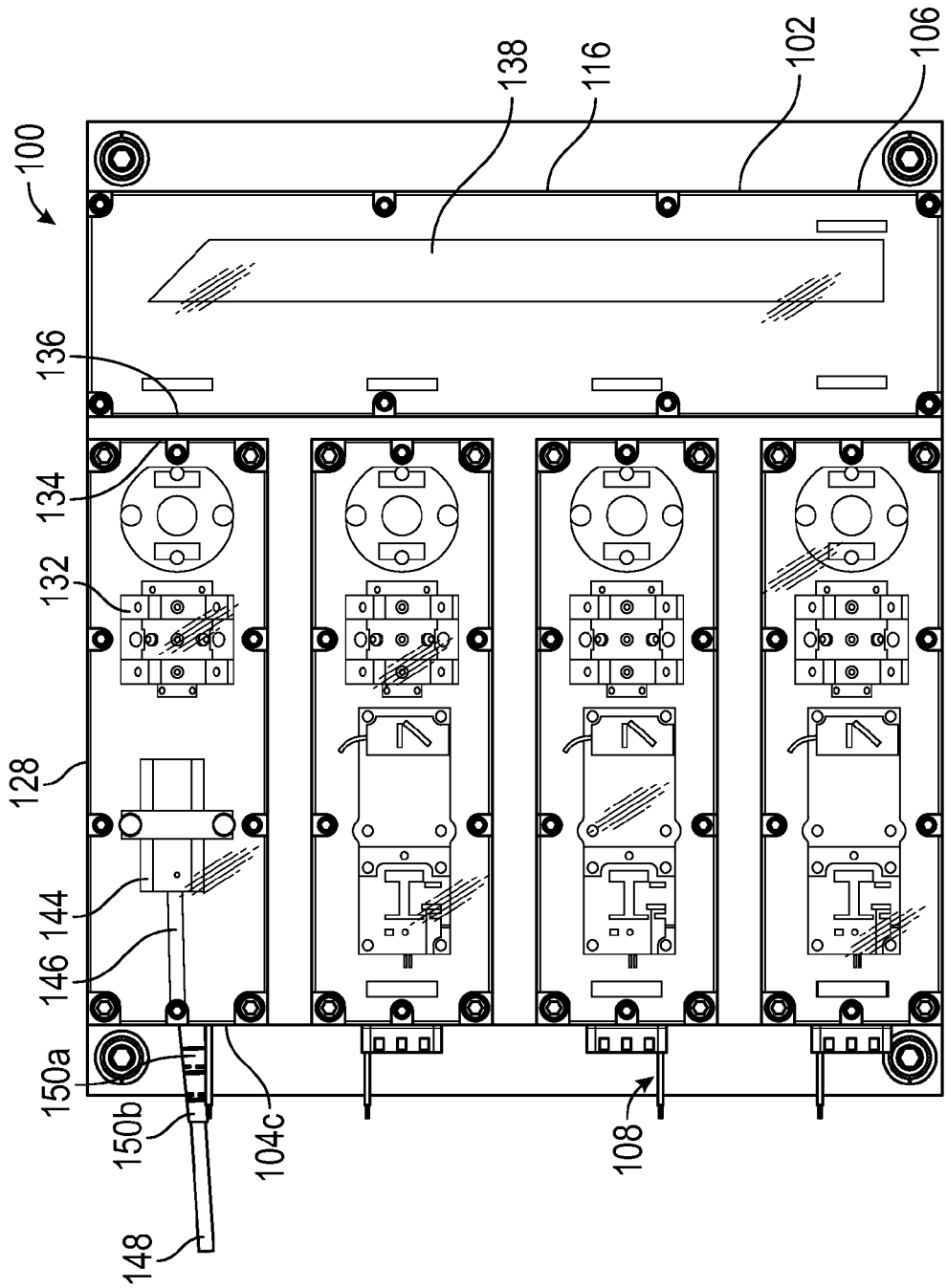
FIG. 16 is a top view of the optical system of FIG. 15.

FIG. 15 is a perspective view of another example embodiment of an optical system 100. FIG. 16 is a top view of the optical system 100 of FIG. 15. With reference to FIGS. 15 and 16, in some embodiments, the base unit 102 (e.g., the enclosure 116) does not include alignment adjustment optical components 152 (e.g., horizontal boresight adjusters) or alignment adjustment interfaces 154. In some embodiments, the optical system 100 can be used for applications in which the acceptable tolerance in the alignment of the light beams can be achieved without the adjustments enabled by the alignment adjustment optical components 152 and alignment adjustment interfaces 154 disclosed herein.

Many variations are possible. For example, in some embodiments, the base unit 102 does not include a thermally stable enclosure 116. For example, in some implementations, the area containing the one or more redirecting optical components 138 (e.g., beam combiner prism) is not temperature controlled. For example, the temperature controller 108 can be configured to transfer heat to control the temperature of the cartridge enclosures 128 but not the base unit enclosure 116. In some embodiments, the one or more redirecting optical components 138 (e.g., beam combiner prism) are not contained within an enclosure on the base unit 102. In some instances, the base unit 102 can include a platform that is configured to support the cartridges 104a-d and/or the one or more redirecting optical components 138 (e.g., beam combiner prism).

Configurations other than those described herein are possible. The structures, devices, systems, and methods may include additional components, features, and steps. In some embodiments, certain of the disclosed components, features, and steps may be excluded and may or may not be replaced with others. Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure (including the '949 Publication and the '054 Publication), in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

What is claimed is:

1. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge;
one or more optical components configured to output a beam of light and disposed in the thermally stable enclosure of the cartridge; and
one or more alignment adjustment optical components disposed in the thermally stable enclosure of the base unit and configured to adjust the alignment of the light beam.

2. The optical system of claim 1, wherein the one or more alignment adjustment optical components can move to adjust the alignment of the light beam in response to an alignment adjustment interface that is accessible from outside the thermally stable enclosure of the base unit.

3. The optical system of claim 2, wherein the alignment adjustment interface comprises a rotatable element.

4. The optical system of claim 1, wherein the one or more alignment adjustment optical components comprises a horizontal boresight adjuster.

5. The optical system of claim 4, where the horizontal boresight adjuster comprises a prism rotatable about a vertical axis.

6. The optical system of claim 4, wherein the one or more alignment adjustment optical components comprises a vertical boresight adjuster.

7. The optical system of claim 1, wherein the one or more alignment adjustment optical components comprises a two axis boresight adjuster.

8. The optical system of claim 1, wherein the one or more alignment adjustment optical components comprises a Risley prism assembly, one or more parallel plates, or combinations thereof.

9. The optical system of claim 1, wherein the one or more alignment adjustment optical components are configured to adjust the alignment of the light beam by up to about plus or minus five milliradians.

10. The optical system of claim 9, wherein the one or more alignment adjustment optical components are configured to adjust the alignment of the light beam by at least about plus or minus 0.1 milliradians.

11. The optical system of claim 1, wherein the one or more alignment adjustment optical components are configured to adjust the alignment of the light beam by up to about plus or minus 0.5 milliradians.

12. The optical system of claim 11, wherein the one or more alignment adjustment optical components are configured to adjust the alignment of the light beam by at least about plus or minus 0.1 milliradians.

13. An optical system comprising:
a base unit having a thermally stable enclosure and a cartridge receiver:
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge;
one or more optical components configured to output a beam of light and disposed in the thermally stable enclosure of the cartridge; and
a second cartridge removably attached to the cartridge receiver.

14. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge; and
one or more optical components configured to output a beam of light and disposed in the thermally stable enclosure of the cartridge;
wherein the one or more optical components configured to output a beam of light and disposed in the thermally stable enclosure of the cartridge comprises a laser.

15. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge; and
one or more optical components configured to output a beam of light and disposed in the thermally stable enclosure of the cartridge;
wherein the one or more optical components configured to output a beam of light and disposed in the thermally stable enclosure of the cartridge comprises a laser diode, a diode-pumped solid-state (DPSS) laser, a fiber laser, or a collimated fiber-coupled laser.

16. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge; and
one or more optical components configured to output a beam of light and disposed in the thermally stable enclosure of the cartridge;
wherein the one or more optical components configured to output a beam of light and disposed in the thermally stable enclosure of the cartridge comprises a fiber optic device.

17. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge; and
one or more optical components configured to output a beam of light and disposed in the thermally stable enclosure of the cartridge;
wherein the one or more optical components configured to output a beam of light and disposed in the thermally stable enclosure of the cartridge comprises a light-emitting diode (LED).

18. An optical system comprising:
a base unit having a thermally stable enclosure and a cartridge receiver;
a cartridge removably attached to the cartridge receiver, the cartridge comprising thermally stable enclosure;
a temperature controller configured to control the temperature in the their rally stable enclosure of the base unit and configured to control the temperature in the thermally stable enclosure of the cartridge; and
one or more optical components configured to output a beam of light and disposed in the thermally stable enclosure of the cartridge;
wherein the one or more optical components configured to output a beam of light and disposed in the thermally stable enclosure of the cartridge comprises a Risley prism assembly, one or more plane parallel plates, or combinations thereof.

19. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge;
one or more optical components configured to output a beam of light and disposed in the thermally stable enclosure of the cartridge; and
one or more optical components configured to output a beam of light and disposed in the thermally stable enclosure of the base unit.

20. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge;
one or more optical components configured to output a beam of light and disposed in the thermally stable enclosure of the cartridge; and
one or more light redirecting optical components configured to redirect the beam of light, wherein the one or more light redirecting optical components are disposed in the thermally stable enclosure of the base unit.

21. The optical system of claim 20, wherein the one or more light redirecting optical components comprises a monolithic beam combiner prism.

22. The optical system of claim 20, wherein the one or more light redirecting optical components comprises one or more dichroic mirrors.

23. The optical system of claim 20, wherein the one or more light redirecting optical components are configured to combine a plurality of light beams.

24. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally, stable enclosure of the base unit and configured to control the temperature in the thermally stable enclosure of the cartridge; and
one or more optical components configured to output a beam of light and disposed in the thermally stable enclosure of the cartridge;
wherein the cartridge further comprising electronic circuitry configured to control a laser.

25. An optical system comprising:
a base unit having a thermally stable enclosure and a cartridge receiver;
a cartridge removably attached to the cartridge receiver, the cartridge comprising a thermally stable enclosure;
a temperature controller configured to control the temperature in the thermally stable enclosure of the base unit and configured to control the temperature in the thermally stable enclosure of the cartridge;
one or more optical components configured to output a beam of light and disposed in the thermally stable enclosure of the cartridge; and
one or more springs configured to removably attach the cartridge to the base unit.

* * * * *